United States Patent [19]
Anderson et al.

[11] Patent Number: 5,884,226
[45] Date of Patent: Mar. 16, 1999

[54] SYSTEM AND METHOD FOR MODELLING MODERATE RESOLUTION ATMOSPHERIC PROPAGATION

[75] Inventors: Gail P. Anderson, Concord; James H. Chetwynd, Stoneham; Lawrence S. Bernstein, Lexington; Alexander Berk, Sharon; Prabhat K. Acharya, Burlington; David C. Robertson, Bedford, all of Mass.; Eric P. Shettle, Chevy Chase, Md.

[73] Assignee: The United States of America as represented by the Secretary of the Air Force, Washington, D.C.

[21] Appl. No.: 867,966

[22] Filed: Jun. 3, 1997

Related U.S. Application Data

[60] Provisional application No. 60/030,426, Oct. 25, 1996.
[51] Int. Cl.[6] .................................................. G06F 169/00
[52] U.S. Cl. .................................................................. 702/3
[58] Field of Search ............................ 702/2–4; 340/601, 340/602; 342/26, 460; 706/931

[56] References Cited

PUBLICATIONS

Arulmani et al., "Water Vapor and SST Retrievals From ATSR Data", Geoscience and Remote Sensing Symposium, 1995; 10–14 Jul. 1995, vol. 2, pp. 890–892

Liang et al., "Angular Characteristics of the Pathfinder AVHRR Land Thermal Data and Radiative Transfer Modeling", Geoscience and Remote Sensing Symposium, 1994; 8–12 Aug. 1994, vol. 1, pp. 61–63.

Kaufman et al., "Remote Sensing of Water Vapor in the Near IR from EOS/MODIS", Geoscience and Remote Sensing, IEEE Transaction on; Sep. 1992, vol. 30, Iss. 5, pp. 871–884.

*Primary Examiner*—Donald E. McElheny, Jr.
*Attorney, Agent, or Firm*—William G. Auton

[57] ABSTRACT

Recent upgrades to the MOTRAN atmospheric radiation code improve the accuracy of its radiance predictions, especially in the presence of clouds and thick aerosols, and for multiple scattering in regions of strong molecular line absorption. MODTRAN3.5 features a generalized specification of cloud properties, while research version MODTRAN4 implements a Correlated-k (CK) approach for more accurate calculation of multiply scattered radiance. Comparisons to cloud measurements demonstrate the viability of the CK approach. The impact of these upgrades on predictions for AVIRIS viewing scenarios is discussed for both clear and clouded skies; the CK approach provides refined predictions for AVIRIS nadir and near-nadir viewing.

13 Claims, 5 Drawing Sheets

Microfiche Appendix Included
(12 Microfiche, 1085 Pages)

FIG. 5

SYSTEM AND METHOD FOR MODELLING MODERATE RESOLUTION ATMOSPHERIC PROPAGATION

STATEMENT OF GOVERNMENT INTEREST

The invention described herein may be manufactured and used by or for the Government for governmental purposes without the payment of any royalty hereon.

CROSS-REFERENCE TO RELATED APPLICATION

The present invention includes the subject matter of the provisional application Ser. No. 60/030,426 filed on 25 Oct. 1996.

REFERENCE TO MICROFICHE APPENDIX

Reference is made to the microfiche appendix which contains 12 sheets and 1085 frames of the MODTRAN4 source code.

BACKGROUND OF THE INVENTION

The present invention relates generally to systems which calculate the effects of the atmosphere on the transmission of radio and optical beams, and more specifically to a moderate resolution propagation model (and system) of the earth's atmosphere. This model can be used for predicting atmospheric transmittance and background radiance from 0 to 50,000 $cm^{-1}$ at a resolution of 2 $cm^{-1}$.

The interest in atmospheric transmittance and background radiance along with the associated subject of astronomical refraction goes back to Laplace. With the advent of large telescopes and phase array radar systems, this interest has become ubiquitous, since the output signals of these systems experience attenuation due to atmospheric particles, water vapor and other gases along the viewing path.

The transmittance and radiance along a path through the atmosphere depend upon the total amount and the distribution of the absorbing and scattering species as well as the variation of pressure and temperature along the path. The integrated amount of absorber or scatterer along a path is known by various names, including "column density," "equivalent absorber amount," and "air mass." While the term "air mass" applies specifically to the total amount of gas along the path, it will be used here to refer loosely to the integrated amounts for all the different species relative to the amount for a vertical path.

The task of ascertaining atmospheric transmittance and atmospheric background radiance is alleviated, to some extent by the systems disclosed in the following U.S. Patents, the disclosures of which are incorporated herein by reference:

U.S. Pat. No. 5,315,513 issued to Abreu et al;
U.S. Pat. No. 5,075,856 issued to Kneizys et al;
U.S. Pat. No. 4,611,929 issued to Holyer;
U.S. Pat. No. 4,661,907 issued to Arnone et al; and
U.S. Pat. No. 4,521,861 issued to Logan et al.

The last three references disclose alternative atmospheric model systems. The first two patents are for the MODTRAN and LOWTRAN models that are improved by this invention. The closest reference is the Abreu et al patent, which uses an earlier model that lack the specific features specified below.

Perhaps the most significant of the above-cited references are the Kneizys and Abreu patents, which were filed for the LOWTRAN 7 and MODTRAN models of the atmosphere, which are discussed below. The Holyer reference discloses a satellite method for measuring sea surface temperature which utilizes LOWTRAN 5, which is a predecessor of the present invention.

In February of 1980, the Phillips Laboratory of Hanscom Air Force Base, Massachusetts developed LOWTRAN5, a Fortran computer code designed to calculate atmospheric transmittance and radiance for a given atmospheric path at low spectral resolution. The details of LOWTRAN 5 are described in a technical report by F. Kneizys et al entitled "Atmospheric Transmittance/Radiance; Computer Code LOWTRAN 5, AFGL-TR-80-0067," the disclosure of which is incorporated herein by reference. This report is available from the National Technical Information Service where it is identified as document number ADA088215.

In LOWTRAN 5, 6 and 7, the atmosphere is modeled as a set of spherically symmetric shells with discrete boundaries. The temperature, pressure, and absorber (gas and aerosol) densities are specified at the layer boundaries. Between boundaries, the temperature profile is assumed linear while the pressure and densities are assumed to follow exponential profiles.

LOWTRAN 6 was developed and described in August 1983 in a technical report entitled "Atmospheric Transmittance/Radiance; Computer Code LOWTRAN 6, AFGL-TR-83-0187," the disclosure of which is incorporated herein by reference. This report is available from the National Technical Information Service, where it is identified as document number ADA137796.

LOWTRAN 6 was an improvement over the previous model LOWTRAN 5, which assumed that the index of refraction was constant between layer boundaries. LOWTRAN 6 assumes a continuous profile for the refractive index, with an exponential profile between layer boundaries. It is more accurate than the previous models and works for all paths.

The LOWTRAN 7 model and computer code calculates atmospheric transmittance and background radiance for a given atmospheric path at low spectral resolution. This version is an extension and update of the current code, LOWTRAN 6 (and its predecessors LOWTRAN 5, LOWTRAN 4, LOWTRAN 3 and LOWTRAN 2). All the options and capabilities of the LOWTRAN 6 code have been retained, but additional refinements have been added, as described below.

The LOWTRAN 7 code calculates atmospheric transmittance, atmospheric background radiance, single scattered solar and lunar radiance, direct solar irradiance, and multiple scattered solar and thermal radiance. The spectral resolution of the model is 20 $cm^{-1}$ (full width at half-maximum) in steps of 5 $cm^{-1}$ from 0 to 50,000 $cm^{-1}$ (0.2 um to infinity). A single parameter band model is used for molecular line absorption and the effects of molecular continuum-type absorption; molecular scattering, aerosol and hydrometer absorption and scattering are included. Refraction and earth curvature are considered in the calculation of the atmospheric slant path and attenuation amounts along the path. Representative atmospheric, aerosol, cloud, and rain models are provided in the code with options to replace them with user-provided theoretical or measured values.

But now LOWTRAN 7 has been displaced by its progeny—MODTRAN—with a current combined (AF and ONTAR) distribution to over 1000 users. The basic advantages of MODTRAN center on the improved spectral resolution and compatibility with HITRAN in its most recent issue ('92 and '95 for MODTRAN2 and 3, respectively).

The most important generic message, however, is that most cases, all LOWTRAN versions should be replaced by MODTRAN.

Because MODTRAN3 is now undergoing external release in mid-1995 (alone with its ONTAR PC version), its advantages are restated here. The primary changes from older versions include: (1) a new solar irradiance, at 1 $cm^{-1}$ resolution (first suggested by B.-C. Gao and developed by R. Kurucz); (2) an alternate multiple scattering algorithm based on DISORT (3) parameter statement control over the total number of atmospheric layers, facilitating user control over the degree of accuracy in replicating atmospheric structure (4) new IP and UV temperature dependent cross sections and (5) improved band model and radiance algorithms, developed and validated against LBL calculations. Subsequent modifications will be made to MODTRAN as they become available. For instance, a new measurement-based solar irradiance (from Shuttle measurements from the 1992 ATLAS campaign, expected in 1995) will be provided, along with the existing options.

Coupled with all previous descriptions of MODTRAN capabilities, MODTRAN3 calculations are demonstrating a breadth of unique applications. In a series of papers, led by the work of J.-M. Theriault, preliminary use of MODTRAN for analysis of moderate resolution interferometer data has been established. These papers did not advocate using MODTRAN alone as the forward radiance algorithm, but, rather, showed that MODTRAN could be employed to obtain the large derivative matrices used in physical inversion algorithms. Because these matrix elements are calculated from determining the sensitivity of small single layer perturbations of each detectable species upon the full path radiance, the near equivalence of the individual matrix elements to those derived analytically from LBL codes was unexpected.

This set of studies did not recommend that the iterative least squares minimization test of forward calculation vs. measurement employ MODTRAN. That recommendation can only be made after careful analyses of the impact of spectral resolution (and its accuracy) on vertical resolution and instrument signal to noise and other error sources. Such studies are currently being undertaken.

A direct outgrowth of the sensitivity of the matrix elements was the suggestion that the MODTRAN layer-specific optical properties (effective optical depth and transmittance/radiance differentials; that is, those quantities derived from differences and ratios of adjacent full path BM calculations) were essentially equivalent to the LBL direct layer calculations. Given the near linearity of this sensitivity, MODTRAN became a candidate for flux-divergence and energy deposition calculations.

The WMO InterComparison of Radiation Codes used in Climate Models (ICRCCM) had already established the basis for evaluation of LBL codes, so MODTRAN was tested against these evaluations. Initial work by L. Kimball, L. Bernstein, and colleagues has now confirmed that with appropriate modifications (an improved radiance algorithm, implemented in MODTRAN3, and introduction of the mathematics to reduce spherical geometry to the "flat earth" approximation of ICRCCM), the IR spectrally integrated (0–3000 $cm^{-1}$) cooling rates for $H_2O$, $CO_2$, and $O_3$ fall within the range of the LBL codes participating in the initial studies.

For two specific examples of a newer ICRCCM comparison (R. Ellingson, private communication) for MODTRAN3 and FASCODE; the measurements are from the AERI, a well-calibrated, surface-based interferometer developed by the Univ. of Wisconsin. In each case the results have been degraded to 10 $cm^{-1}$ resolution and subsequently compared to the ICRCCM standard radiative transfer model: LBL-RTM. While the statistics appear to slightly favor FASCODE over LBLRTM, in general (and for the 4 ICRCCM cases), LBLRTM and FASCODE are relatively indistinguishable, although the DOE-funded effort has made much progress in both computational efficiency and upgraded spectral sampling (resulting in improvements to better than 1%, not distinguishable on this scale. This agreement is not unreasonable in that both codes have a common lineage. The important aspect is that these two line-by-line codes (and the next generation, FASE) share the best agreement with the ICRCCM measurement set, approximately 2–3% mean difference and 4–6% rms difference (with values beyond 2400 $cm^{-1}$ dropped because of extremely low S/N). The comparable statistics for MODTRAN are approximately twice as large, 5–10% mean and 6–12% rms. The difference in the statistical errors between MODTRAN and the line-by-line codes can also be seen in any direct comparison of their calculations, whether in transmittance or radiance; MODTRAN residuals are usually within a few percent of exact calculations, and every attempt is being made to reduce this magnitude.

Another recent example of validation of both FASCODE and MODTRAN also employs a Univ. of Wisconsin measurement set derived from their airborne instrument: HIS. A small spectral range (2000–2700 $cm^{-1}$) of a measurement was taken from the NASA ER-2 over the Eastern Pacific. This spectral band has been chosen because it demonstrates the overlap in the thermal and solar Planck functions. The residual between measurement and FASCODE longward of 2400 $cm^{-1}$ is due to reflected solar contributions. Putting in a minimum surface albedo of 0.05 and employing the MODTRAN solar capability reduces this residual between measurement and model almost completely. The virtue of having a single model with full thermal and solar radiation fields is quite apparent.

Given this success and general agreement with the LBL spectral cooling rate distributions for $H_2O$ calculated by Clough et al., a more general energy deposition study has been undertaken. Again, the "flat earth" assumption has been maintained but otherwise a preliminary version of MODTRAN3 (missing only the new solar irradiance and the DISORT algorithm) was used for all calculations. The code was run from 0 to 50,000 $cm^{-1}$ in two modes: (1) radiance with single scattering (which includes both thermal and solar sources), and (2) direct solar irradiance. A typical pair of up- and down-welling radiances for the full path at 15 km, might be measured from an aircraft flying at the tropical tropopause. The direct solar contribution is omitted and the assumed surface albedo is 0.1. Similar radiance calculations were done for 4 quadrature angles at each of 60 layer boundaries to approximate the $2\pi$ fluxes while the approximations for daily averaged solar insolation were based upon a single solar incidence angle weighted for day of year (120) and latitude (tropical, 15N). An actual energy budget as determined from measurement, would also be the end result of complex sets of integrated data and spectral syntheses, no single instrument being able to provide the spectrally appropriate up- and down-welling contributions over the entire spectral range. Of course, this preliminary demonstration can only begin to provide estimates of sensitivities, even when validating data are available.

Characterization of surface properties from AVIRIS measurements is hampered by atmospheric attenuation and path radiances. MODTRAN, the Air Force PL/Geophysics Directorate moderate spectral resolution (2 cm$^{-1}$) background radiance and transmission model, is often used to account for the atmospherics in AVIRIS measurements. It rapidly predicts the molecular and aerosol/cloud emissive and scattered contributions to observed radiances along with the atmospheric attenuation. MODTRAN has been extensively validated against both measurements and the high spectral resolution FASCODE model.

In view of the foregoing discussion, it is apparent that there remains an ongoing need to obtain refined estimates of atmospheric transmittance and background radiance, and that state-of-the-art methods are literally adapted for use almost as fast as they are developed by users that include the United States Air Force and other DOD agencies. The present invention is intended to satisfy that need.

SUMMARY OF THE INVENTION

The present invention is implemented in a computer program entitled MODTRAN 4.0, which is contained in the attached microfiche appendix, and which operates when loaded into a computer. MODTRAN is a moderate resolution model of the earth's atmosphere and computer code used to predict atmospheric transmittance and background radiance in the microwave, infrared, visible and near ultraviolet spectral regions (0 to 50,000 cm$^{-1}$ or 0.2 um to infinity). The code maintains complete computability with LOWTRAN 7 and all the earlier versions of MODTRAN. MODTRAN 4.0 has the following improvements over the previous MODTRAN and LOWTRAN patents: an improved approach for treating multiple scattering in the presence of molecular absorption lines using a correlated-k (CK) capability; a Monte-Carlo line-by-line spectral simulation is used to generate CK absorption coefficient distributions; a compact data base representation of CK distributions is included for real time MODTRAN calculations; the CK approach is used for rapid calculation of atmospheric radiative heating and cooling rates for both clear and cloudy conditions; and include both thermal and solar contributions.

The process continues with a calculating step in which the atmospheric transmittance and background radiance is calculated. Finally, the process ends with an output step in which the atmospheric transmittance and background radiance is output along with the conditions selected in the input step.

In one embodiment of the invention, the calculating step is performed using a computer which contains a plurality of reference atmospheres which each define atmospheric temperature, pressure and density as a function of altitude. The computer serves as a means for calculating atmospheric transmittance and atmospheric background radiance and may function without external sensors (which provide measured values of temperature, pressure and density).

It is a principal object of the present invention to provide a moderate resolution propagation model for predicting atmospheric transmittance and background radiance to users of systems that include uv, visible, microwave and infrared tracking systems, communication systems, and satellite weather sensing systems.

It is another object of the present invention to provide a refined estimate of transmittance and multiple scattered radiation using an atmospheric data base that includes molecular profiles for thirteen minor and trace gases, and six reference atmospheric models that define temperature, pressure and density, as a function of altitude, and a number of models for the atmospheric aerosols, clouds and rain.

It is another object of the present invention to calculate the effects of weather on the transmission of infrared and optical beams.

These objects together with other objects, features and advantages of the invention will become more readily apparent from the following detailed description when taken in conjunction with the accompanying drawings wherein like elements are given like reference materials throughout.

DETAILED DESCRIPTION OF THE PREFERRED EMBODIMENT

The present invention includes a moderate resolution propagation model and system for predicting atmospheric transmittance, background radiance, and contains two new features which greatly improve predictive capabilities under cloudy and/or heavy aerosol loading conditions. It allows a user to explicitly define water and ice cloud vertical profiles and spectral data either by scaling the default model clouds or by defining a new model cloud.

MODTRAN4 also introduces a Correlated-k (CK) capability which significantly improves the accuracy of the multiple scattering radiance calculations. In the following, a discussion of the MODTRAN4 upgrades and an initial validation by comparison to airborne measurements of a solar illuminated cumulus cloud top are presented.

The present invention is implemented in the computer code in the microfiche appendix, which can be run on any computer capable of operating in FORTRAN. This new code is called MODTRAN4. The LOWTRAN transmittance model and associated subroutines have been fully integrated into MODTRAN, and all the LOWTRAN 7 options, i.e., aerosol models, atmospheric paths, transmittance/radiance, user-specified data, etc., have been maintained.

In operation MODTRAN4 may rely on physical sensors to provide weather data as input in a determination of atmospheric transmittance and background radiance to an infrared system, or a system analogous to the U.S. Navy's satellite temperature measurement system of the above-cited Holyer patent. The present invention can be regarded as a process for providing a moderate resolution propagation model and for predicting atmospheric transmittance and background radiance. The process begins with an inputting step in which desired choices are made to define conditions under which the atmospheric transmittance and background radiance will be predicted. These conditions include: a choice of model atmosphere, a path of interest through the atmosphere, a spectral region of interest, and a level of spectral resolution that can range between about 20 and 2 cm$^{-1}$.

Characterization of surface properties from AVIRIS measurements is hampered by atmospheric attenuation and path radiance's, the Air Force PL/Geophysics Directorate moderate spectral resolution (2 cm$^{-1}$) background radiance and transmission model, is often used to account for the atmospherics in AVIRIS measurements. It rapidly predicts the molecular and aerosol/cloud emissive and scattered contributions to observed radiances along with the atmospheric attenuation. MODTRAN has been extensively validated against both measurements and the high spectral resolution FASCODE (Clough et al., 1988) model.

MODTRAN4, currently under development, contains two new features which greatly improve predictive capabilities under cloudy and/or heavy aerosol loading conditions. It allows a user to explicitly define water and ice cloud vertical profiles and spectral data either by scaling the default model clouds or by defining a new model cloud.

MODTRAN4 also introduces a Correlated-k (CK) capability which significantly improves the accuracy of the multiple scattering radiance calculations. In the following sections, a discussion of the MODTRAN4 upgrades and an initial validation by comparison to airborne measurements of a solar illuminated cumulus cloud top are presented. Finally, the effect of the CK approach for two AVIRIS scenarios is demonstrated.

The MODTRAN cloud/rain models have been upgraded and now allow for generalized specification of layering and optical and physical properties as well as the presence of multiple overlapping and non-overlapping clouds. The cloud models affected are all of the cumulus and stratus type clouds, both with and without rain. This includes MODTRAN cloud/rain models 1 through 10. The cirrus models 17–19 only required improved layering. The cloud model upgrades include:

adjustable cloud parameters,
thickness, altitude, vertical extinction, column amounts, humidity, and scattering phase functions,
decoupling of the clouds from aerosols,
introduction of ice particles,
user-defined water droplet, ice particle and rain rate profiles,
user-defined cloud spectral properties, and
output of cloud/rain profiles and spectral data to tape6 (NOPRT=-1).

The decoupling of the cloud and aerosol models has a number of implications. Clouds and aerosols can co-exist at a single altitude, or clouds can be modeled with no aerosol profiles included. When clouds and aerosols co-exist, the cloud water droplets, cloud ice particles and aerosol particles may all have different scattering phase functions. The single scatter solar contribution of each component is properly combined. However, for multiple scaattering, a single effective phase function is defined based on a scatteering optical depth weighted Henyey-Greenstein asymmetry factor; this is the same approach that is used to combine the aerosol and molecular scattering contributions.

Addition of a CK capability to MODTRAN provides an accurate and fast means for evaluation of the effects of clouds and heavy aerosol loading on retrievals (both surface properties and species concentration profiles) and on atmospheric radiative heating/cooling calculations. These radiative transfer computations require coupling the effects of gaseous molecular absorption due primarily to water vapor, carbon dioxide, and ozone, with particulate multiple scattering due to volcanic aerosols, ice crystals and water droplets. The molecular absorption band model used in MODTRAN is not suitable for interfacing with standard multiple scattering algorithms. This is because the scattering models require a monochromatic representation of the molecular transmission (i.e., Beer's law), whereas molecular band models which represent the transmission for a finite spectral interval do not follow Beer's law. In order to adapt a band model approach for use in scattering calculations it is necessary to express the band model transmission function in terms of a weighted sum of Beer's law exponential terms. Thus, a method for determining the weighing factors and monochromatic absorption coefficients for the MODTRAN band model is required. An abbreviated discussion of the CK approach as tailored for integration into MODTRAN is given below.

For simplicity, consider the problem of determining the average transmittance for a homogeneous path over a finite spectral interval. The generalization to inhomogeneous path is straightforward and is also described below. The path transmittance can be exactly determined through evaluation of:

$$T(u) = \frac{1}{\omega_2 - \omega_1} \int_{\omega_1}^{\omega_2} d\omega \exp(-k(\omega)u). \tag{1}$$

where $\omega$ is frequency, $k(\omega)$ is the monochromatic absorption coefficient, and u is absorber column density. The basis of the CK approach is that evaluation of $T(u)$ by integration over frequency can be replaced by an equivalent integration over the distribution of absorption coefficient values $f(k)$ in the spectral interval $$T(u) = \int_0^\infty dk f(k) \exp(-ku) \tag{2}$$

The difficulty in evaluation of $T(u)$ via Equation (2) is the necessity of first determining $f(k)$; the advantage is that $k(\omega)$ is typically a highly repetitive function of $\omega$ (i.e., there are many nearly equivalent values of a given k in a spectral interval) and thus numerical evaluation of Equation (2) requires far fewer grid points than Equation (1). Note that $f(k)=0$ above the maximum $k_{max}$ and below the minimum $k_{min}$ absorption coefficients in the spectral interval. The probability distribution $f(k)$ can be determined directly from $k(\omega)$ by binning the k's into selected $\Delta k$ sub-intervals.

The distribution function $f(k)$ is not smooth or monotonic; it generally consists of a series of sharp spikes which reflects the sharp-line structure of $k(\omega)$. It then becomes more computationally convenient to work with the smooth and monotonic cumulative probability distribution function $$g(k) = \int_0^k dk' f(k') \tag{3}$$

Physically, $g(k)$ is the fraction of absorption coefficients below k within the finite spectral interval $\omega_1$ to $\omega_2$. It assumes the values $g=0$ at $k=k_{min}$ and $g=1$ at $k=k_{max}$. The transmittance is related to g by $$T(u) = \int^1 dg \exp(-k(g)u) \tag{4}$$

where $k(g)$ is given by the inverse of $g(k)$, $k(g)=g^{-1}(k)$. In practice, the evaluation of Equation (4) proceeds via summation according to where the $\Delta g_i$'s and $k_i$-s are the sub-interval weighting factors and effective absorption coefficients necessary for the MODTRAN band model. The maximum number of intervals $i_{max}$ and the specific selection of $\Delta g_i$ interval boundaries $(g_i, g_i+1)$ are chosen based on consideration of a number of factors including computational speed and accuracy, and the altitude and spectral ranges of interest. For multi-layer paths it is assumed that there is perfect spectral correlation among the sub-intervals of each layer, resulting in a total path transmittance given by where j denotes the sum over layers.

The MODTRAN band model for a single species (multiple species are discussed later) is based on four parameters: (1) the integrated line strength S in a spectral interval $\Delta\omega$ ($\Delta\omega$=1 cm$^{-1}$ in MODTRAN), (2) the effective number of equivalent lines n (non-integer values of n are acceptable) in the interval, (3) the average pressure broadening Lorentz line width $\gamma_L$, and (4) the Doppler line width $\gamma_D$. These parameters are determined directly from the 1992 HITRAN parameter line compilation (Rothman et al., 1992).

The functional form for the band model transmittance derives from the assumption that all the lines in the spectral interval are positionally uncorrelated and thus accounts for line overlap in a statistically average sense. The transmittance contribution due to the tails of lines which originate from outside the spectral interval are included as a single multiplicative Beer's law term. Detailed formulas for the equivalent width W can be found in Berk et al. (1989). As discussed elsewhere (Bernstein et al., 1995), the k-distribution g(k) for the band model can be determined from line-by-line (LBL) simulations which are physically constrained by the same assumptions used to derive transmittance.

A table of k(g) distributions was constructed for real time use during a MODTRAN run. Each tabulated k(g) distribution corresponds to a specific set of values for n, $\gamma_L$, and $\gamma_D$, and a reference interval strength of S=1 cm$^{-1}$ atm$^{-1}$. The ranges of values considered for these parameters were chosen to be compatible with radiative transfer calculations covering the altitude range of 0–70 km, the spectral range of 10–10,000 cm$^{-1}$, and including all the MODTRAN atmospheric species. This translated into the ranges of 0.2–10$^{-6}$ cm$^{-1}$ for $\gamma_L$, 0.02–10$^{-5}$ cm$^{-1}$ for $\gamma_D$, and 1–90 for n. Each of these ranges was spanned by a logarithmic scale of values with a spacing factor of $2^{1/2}$. This resulted in approximately 10,000 tabulated distributions where each distribution was represented by 33 g values. The overall size of the k(g) data base is 1.4 mbytes. The g values were selected so that the k(g) distribution with the largest dynamic range in k values would have each decade of k values covered by approximately 3 ($k_i$,$g_i$) points. It would be preferable from a computational speed point of view to span each decade with fewer points; however, as shown later, 3 points per decade is a reasonable trade off between computational speed and accuracy. The largest dynamic range occurs for n=1, $\gamma_L$=10$^{-6}$, and $\gamma_D$=10$^{-5}$ cm$^{-1}$. Most of the gi points were selected based on the logarithmic scale $g_i$=1–105 (1.46780)$^i$, where i ranged from 1 to 10. Three additional points were added, g=1 for the peak, g=0.05 and g=0.1 to resolve the structure near g=0.0.

Figure 1:
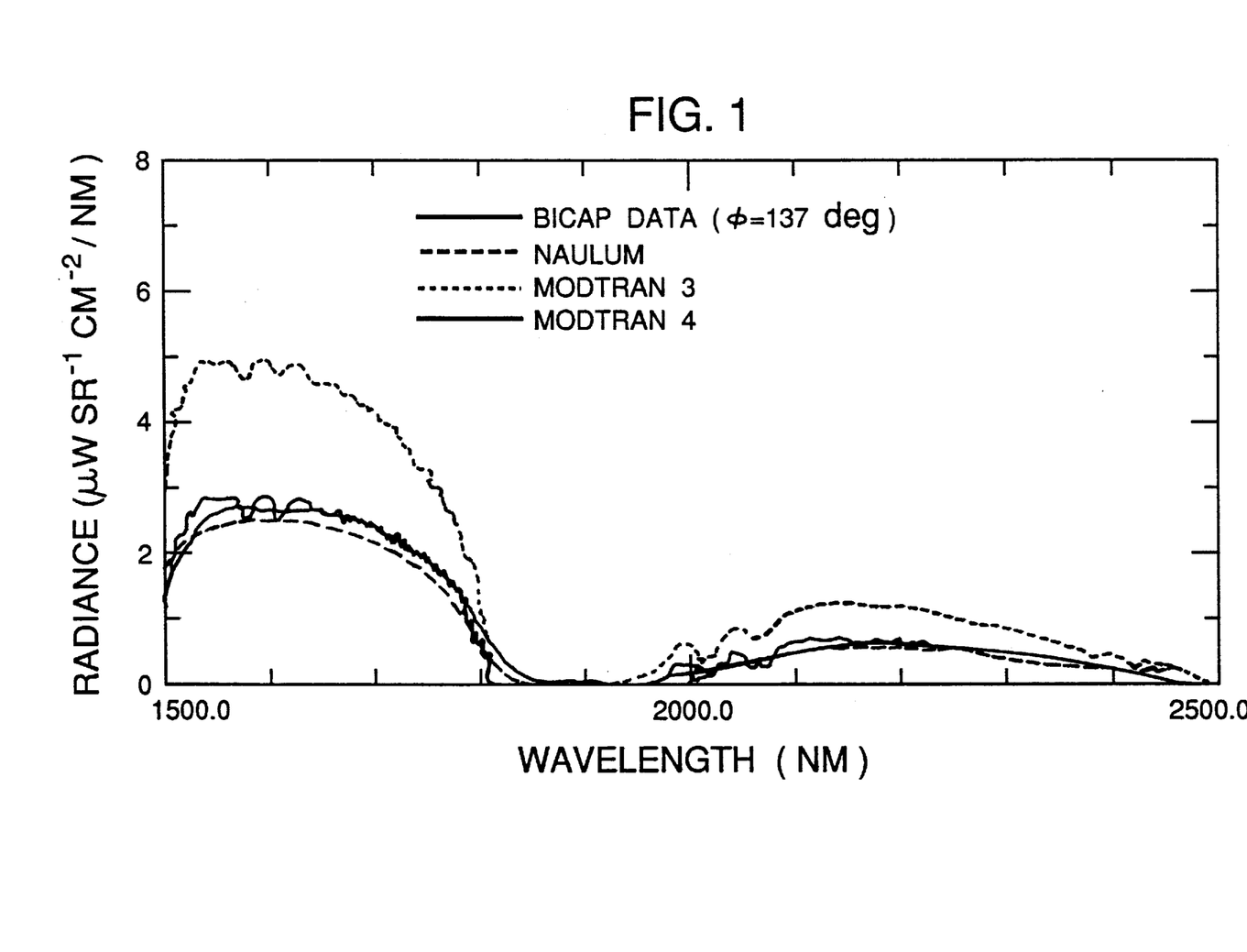
FIG. 1 illustrates a comparison of calculated radiance predictions to airborne measurements performed by ONERA and CELAR using SICAP.

FIG. 1 illustrates a comparison of calculated radiance predictions to airborne measurements performed by ONERA and CELAR using SICAP, a circular variable filter cryogenic spectrometer (1500–5500 nm, 2% spectral resolution). The aircraft altitude was 3.0 km, the cloud top was 2.5 km, the sense or line-of-sight (LOS) zenith angle was 104°, and the solar zenith and relative azimuth angles were 48° and 137°, respectively. Three sets of calculations are shown: (1) results from NAULUM (Malherbe et al., 1995), a new radiative transport model developed at ONERA.

MODTRAN calculations performed with the CK approach (labeled MODTRAN3), and (3) MODTRAN calculations performed with the CK approach (labeled MODTRAN4). The MODTRAN4 cloud model upgrade enabled the cloud profile and spectral data to be explicitly entered for both the MODTRAN3 and MODTRAN4 calculations. The cumulus cloud was modeled with a homogeneous liquid water droplet density of 0.68 g/m$^3$ from 0.1 to 2.5 km altitude. Water droplet single scattering albedos (Hansen et al., 1970) for a mean spherical particle radius of 8 $\mu$m were entered at a 0.05 $\mu$m spectral resolution. Both MODTRAN calculations were performed using a simpler two-stream multiple scattering model (Isaacs et al., 1987); the discrete ordinate model in MODTRAN, DISORT (Stamnes et al., 1988), was run with 8-stream over a limited spectral sub-region and produced similar results. MODTRAN3 severely overpredicts the multiple scattering contributions; this is the expected result because the MODTRAN band model layer single scattering albedos are too large.

Figure 2:
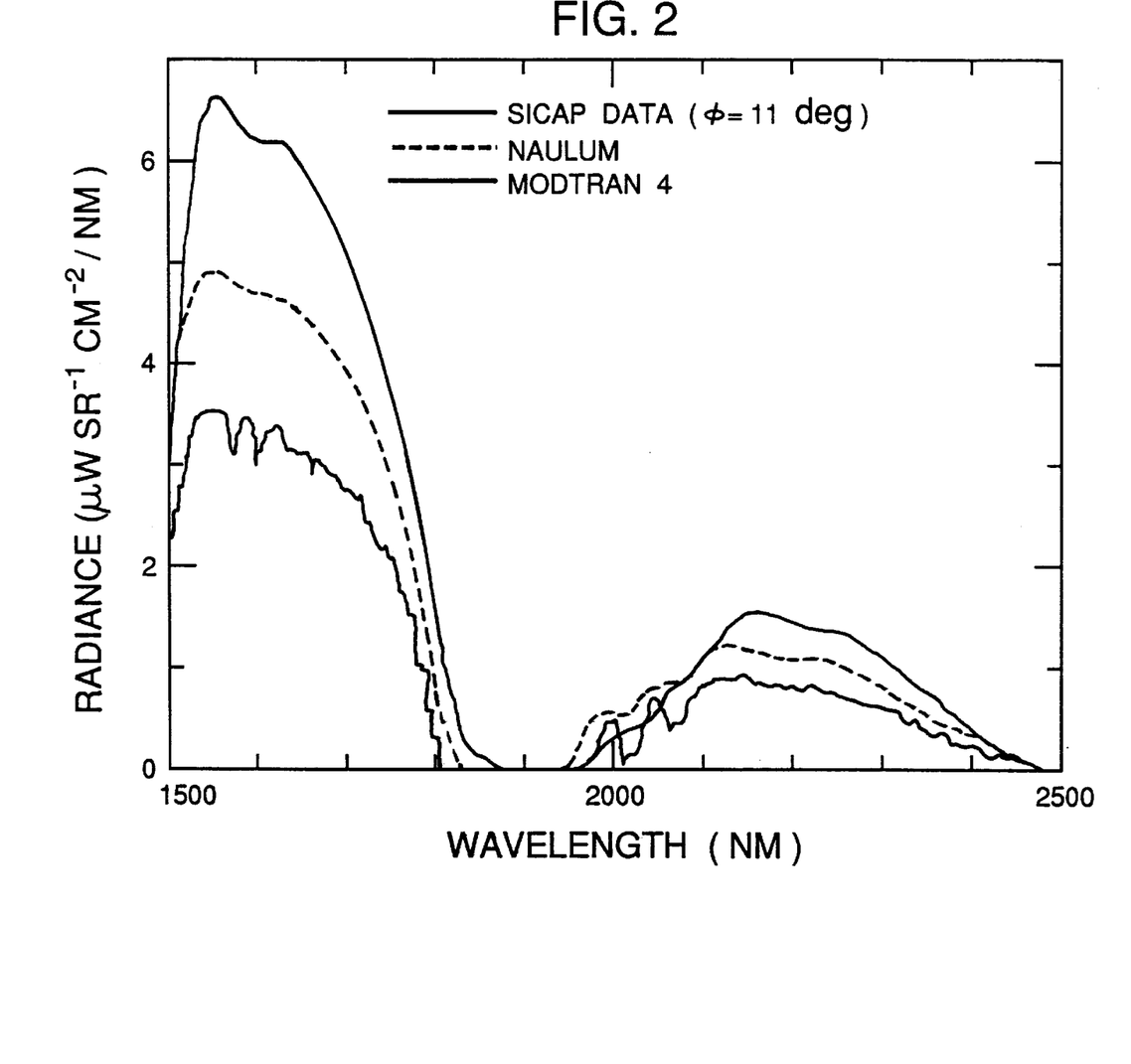
FIG. 2 illustrates an additional comparison of calculated radiances to SICAP, but with a LOS zenith angle of 95° and, more importantly, with a solar relative azimuth angle of 11°.

FIG. 2 illustrates an additional comparison of calculated radiances to SICAP, but with a LOS zenith angle of 95° and, more importantly, with a solar relative azimuth angle of 11°. In this forward scattering case, MODTRAN4 underpredicts the measurements by a factor of 2 because the multiple scattering model averages over the azimuthal dependence (MODTRAN does properly account for the relative azimuth angle in calculation of a single scatter solar but single scatter solar is less than 20% of the total radiance in this example). The better agreement of MODTRAN3 with SICAP measurements results from fortuitous cancellation of errors. The NAULUM calculation is an improvement over MODTRAN4 because it models the azimuthal distribution of radiation in its discrete ordinate multiple scattering calculation. A new version of DISORT has been developed which also models this azimuthal dependence, but this upgrade has not yet been ported to MODTRAN. For the nadir viewing geometries, such as AVIRIS, the neglect of the azimuthal dependence for the multiply scattered photons in DISORT is a reasonable approximation; simularly, the two-stream Issac's model is also expected to yield good results.

Figure 3:
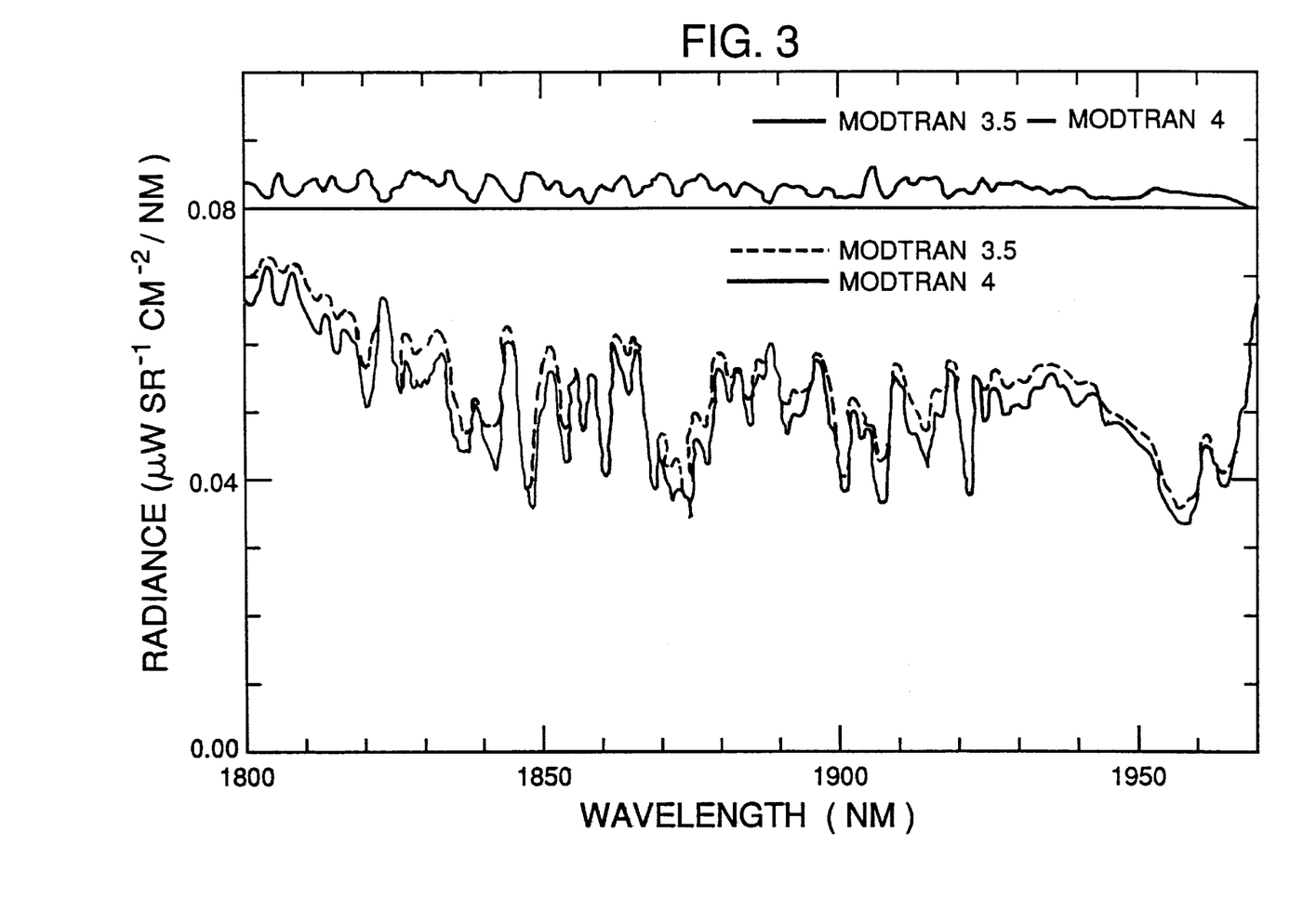
FIG. 3 illustrates differences between the down-looking radiances predicted by MODTRAN3 and MODTRAN4 in the center of the 1.9 $\mu$m H$_2$O band.

The primary focus of AVIRIS is the characterization of the Earth's terrestrial surface. For many applications, the upgrade from MODTRAN3 to MODTRAN4 will have only a minor effect on the analysis of AVIRIS data. Under clear sky or thin cirrus condidtions, differences between MODTRAN3 and MODTRAN4 down-looking radiances from 20 km in the 400 to 2500 nm spectral region are generally small. This will be true whenever multiple scattering is only a small fraction of the total radiance, or whenever spectral variation of molecular absorption is small. However, these conditions are not always satisfied. FIG. 3 illustrates diffeences between the down-looking radiances predicted by MODTRAN3 and MODTRAN4 in the center of the 1.9 $\mu$m H$_2$O band. These calculations were performed with a 1 km thick cirrus cloud at 10 km altitude (0.14 vertical extinction at 550 nm), a solar zenith angle of 75°, and using the MODTRAN grass surface reflectances (Mustard, 1991). Within the 1.9 $\mu$m band region, MODTRAN3 radiances are too high by 0 to 20%.

Figure 4:
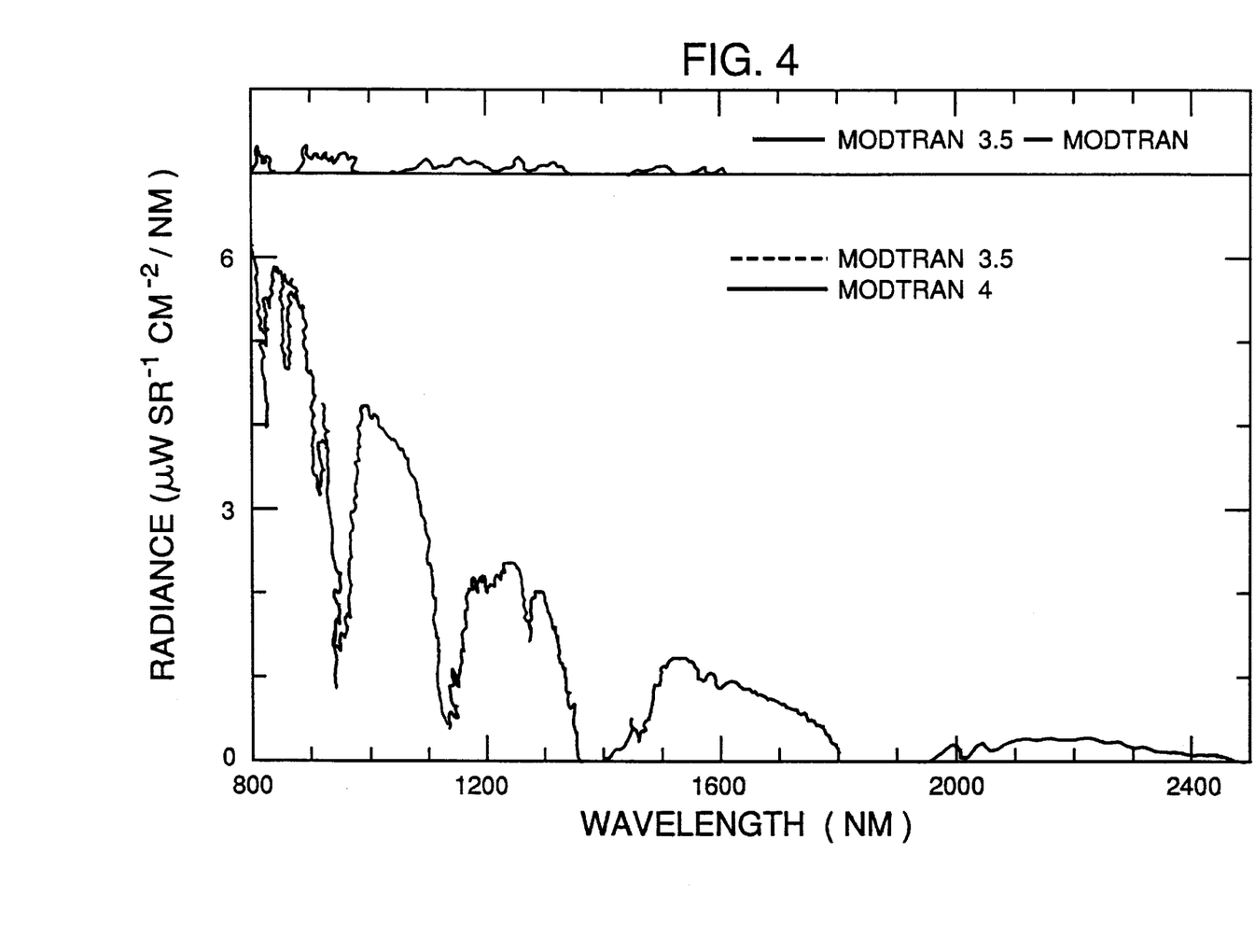
In FIG. 4, MODTRAN 3 and MODTRAN4 mid-IR and near-IR radiances are compared for a nadir view of the MODTRAN model altostratiis cloud (ICLD=2)

For measurements of solar illuminated optically opaque clouds, MODTRAN4 upgrades are critical. In FIG. 4, MODTRAN 3 and MODTRAN4 mid-IR and near-IR radiances are compared for a nadir view of the MODTRAN model altostratus cloud (ICLD=2). The observer is at 20 km altitude and the solar zenith was again set to 75°. The MODTRAN3 radiance predictions are particularly poor in this example; in the center of the H$_2$O bands, the MODTRAN3 overpredicts MODTRAN4 by approximately a factor of two. Outside of the H$_2$O molecular bands, MODTRAN3 is still high, but only by approximately 20%. This example demonstrates the importance of using MODTRAN4 when analyzing AVIRIS measurements of solar scatter off clouds.

Major MODTRAN upgrades have been introduced which lead to significant improvements in the calculation of solar and thermal scattering from clouds and aerosols. The cloud/aerosol models now allow for generalized layering and specification of physical and optical properties. The new CK radiative transfer model leads to more accurate miltiple scattering calculations, particularly in spectral regions containing strong molecular line absorption. It was shown that multiple scattering contributions can be important even for an optically thin solar illuminated cirrus cloud in the NIR-VIS spectral region; thus, these MODTRAN upgrades will lead to improved data analyses and atmospheric/surface property retrievals from down-looking sensors, such as AVIRIS, whose data are often "contaminated" by sub-visual clouds.

"Hyperspectral" is a relatively new descriptor measurement techniques historically usd by the atmospheric remote sensing communities. As opposed to "multi-spectral" sensing, which includes any instrument with a finite number of specific channels, filters, or bands, hyperspectral implies employing enough (usually contiguous) channels to provide a redundant information on both the characteristics of the surface and the atmosphere when the instrument is configured for nadir viewing. This definition (Alex Goetz, Univ. Of Colorado, private communication) can be contrasted with others, such as "any instrument with better than 4 cm$^{-1}$ resolution." This latter definition can be inadequate in the infrared spectral range because many overlapping molecular systems will not be sufficiently discriminated at such 'narrow' resolution. However, the 4 cm$^{-1}$ is often much more than adequate in the visible, when typical resolutions of 10 nm (e.g. AVIRIS, Green et al., 1996) at 600 nm corresponds to a frequency resolution of over 200 cm$^{-1}$.

With the development of MODTRAN4, a flexible tool for applications of realistic hyperspectral sensing is now available. While this version of MODTRAN is grounded in the prior series of AF radiative transfer band model (BM) algorithms (LOWTRAN, Kneizys, et al., 1980, 1983, 1988, through MODTRAN3, Berk et al., 1989, 1995), it is distinct in its ability to employ Beer's law ($T_v$=exp(-k$_{v,i}$n$_i$)) to describe local layer, species-specific transmittance for input to the radiance calculations. While this capability is not always necessary, it allows appropriate handling of multiple scattering (m.s.) using existing non-BM algorithms (DISORT, Stamnes et al., 1988, and Isaacs et al., 1987). MODTRAN4, while maintaining the basic 2 cm$^{-1}$ spectral resolution, can now complement the m.s. routines by introducing a Correlated-k (CK) capability which is expressly compatible with Beer's law formulations. MODTRAN4 also provides greatly improved predictive capabilities under cloudy and/or heavy aerosol loading conditions in both the visible and IR by allowing the explicit definition of water and ice cloud vertical profiles and spectral data, either by scaling and combining default model clouds or by redefining entirely new model clouds with micro-layering options.

It can be shown that this combination of improvements will permit rapid identification of atmospheric contaminants/signatures in window regions as well as accurate spectral calculations of heating/cooling rates in the presence of clouds for both thermal and solar spectral regimes. Finally, in the regions of molecular opacity, where weighting functions peak in the atmosphere, it is expected that MODTRAN4 can play a role in very quick look retrievals, avoiding the large number of line-by-line (LBL) calculations necessary for initiating derivative (perturbation) matrices (Anderson et al., 1993). While the error estimates and residuals associated with a 2 cm$^{-1}$ algorithm will be larger than those associated with LBL retrievals, the speed advantage for image processing might warrant this initial approach.

Figure 5:
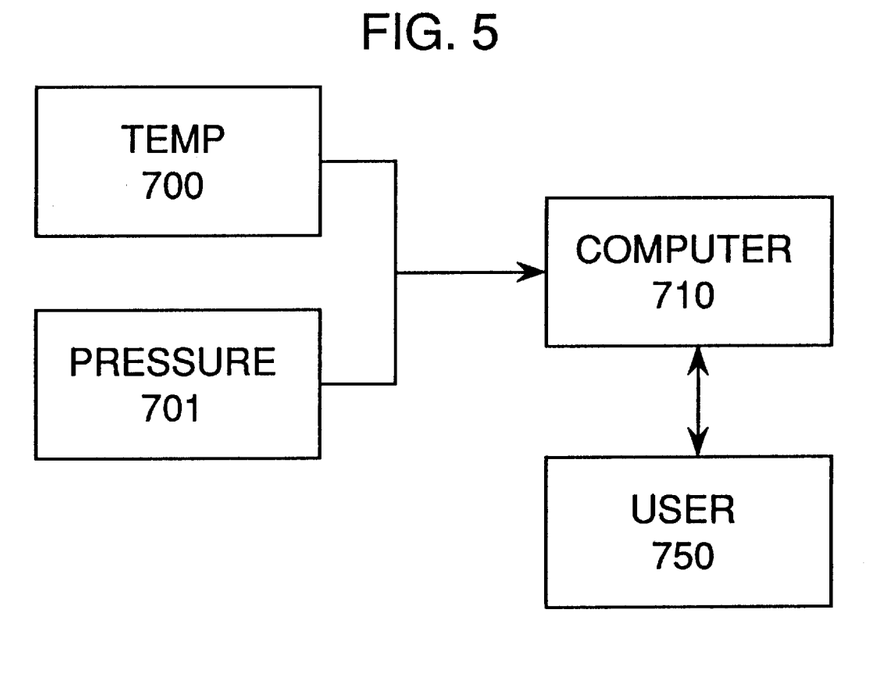
FIG. 5 is a block diagram of a sensor system which uses the present invention.

The reader's attention is now directed towards FIG. 5 which is a block diagram of a system which uses the present invention. The system of FIG. 1 includes: a plurality of external sensors 700 and 701; a computer 710, and a host system 750 which is making use of the present invention.

The computer 710 can be any conventional system which includes a FORTRAN 77 compiler, and which is electrically connected with the external sensors 700 and 701 along with the host system 750. As discussed above, the computer 710 produces an estimate of: atmospheric transmittance; atmospheric background radiance; single and scattered solar and lunar radiance, direct solar irradiance; and multiple scattered solar and thermal radiance for slant angles used by the host system 750. As mentioned above, when the computer 710 is loaded with the MODTRAN programs it can make these calculations using an atmospheric data base which includes molecular profiles for thirteen minor and trace gases, and six reference atmospheres which define atmospheric temperature, pressure and density as a function of altitude.

The user block 750 in FIG. 5 can be the data terminal of any sensor system (such as that of the Holyer patent) or communication system which transmits signals through the atmosphere. Such systems can greatly benefit from the use of MODTRAN. When they input their projected slant angles into the computer 710, they receive in return the estimates of atmospheric transmittance and background radiance, affect such transmitted signals by different amounts. Phased array radar systems that attempt to track remote orbiting objects and determine their radar cross sections can benefit by such estimates when they are aware of the effect of the atmosphere on target echo return signals.

What is claimed:

1. A process for providing a moderate resolution propagation model and for predicting atmospheric transmittance and radiance for a spectral region of interest at a resolution ranging between about 20 cm$^{-1}$ and about 2 cm$^{-1}$, said process comprising the steps of:

defining conditions under which the atmospheric transmittance and background radiance will be predicted, said conditions including a definition of water and ice cloud verticle profiles, a spectral region of interest, and a level of spectral resolution that can range between about 20 and 2 cm$^{-1}$;

selecting band model parameters which comprise an absorption coefficient, a line density value and Lorenz and Doppler line width values for said condition; and calculating said atmospheric transmittance and radiance using said absorption coefficient, said line density value and said line width value.

2. A process, as defined in claim 1, wherein said defining step is performed by scaling default model clouds and defining new cloud models so that said atmospheric transmittance and radiance in said spectral region of interest can be estimated more accurately.

3. A process, as defined in claim 2, wherein said defining step is performed by specifying adjustable cloud parameters that comprise: thickness, altitude, verticle extinction, column amounts, humidity and scattering phase functions.

4. A process, as defined in claim 2, wherein said defining step is performed by specifying user-defined water droplet, ice particle and rain rate profiles from a data base.

5. A process, as defined in claim 2, wherein said defining step is performed by specifying user-defined cloud spectral properties from a data base.

6. A process, as defined in claim 3, using a computer that performs said selecting step using a HITRAN atmospheric data base which has separate cloud/rain profiles for a plurality of spectral characteristic options.

7. A process, as defined in claim 3, using a computer that performs said selecting step using an atmospheric data base which has separate cloud/rain profiles including an option to decouple clouds from aerosols and introduce a presence of ice particles for a plurality of spectral characteristic options.

8. A process, as defined in claim 6, which includes an output step in which the atmospheric transmittance and background radiance is output along with the conditions selected in the input step.

9. A process, as defined in claim 7, which includes an output step in which the atmospheric transmittance and background radiance is output along with the conditions selected in the input step.

10. A process, as defined in claim 1, wherein said calculating step is performed using a computer programmed with a correlated-k capability to calculate effects of clouds and heavy aerosol loading on gaseous molecular absorption and includes an output step in which the atmospheric transmittance and background radiance is output along with the conditions selected in the input step.

11. A process, as defined in claim 2, wherein said calculating step is performed using a computer programmed with a correlated-k capability to calculate effects of clouds and heavy aerosol loading on gaseous molecular absorption and includes an output step in which the atmospheric transmittance and background radiance is output along with the conditions selected in the input step.

12. A process, as defined in claim 3, wherein said calculating step is performed using a computer programmed with a correlated-k capability to calculate effects of clouds and heavy aerosol loading on gaseous molecular absorption and includes an output step in which the atmospheric transmittance and background radiance is output along with the conditions selected in the input step.

13. A moderate resolution atmospheric propagation model comprising:
   a host system which transmits signals through an atmosphere along selected slant angle, outputs a data stream defining said slant angles; and
   a means for calculating atmospheric transmittance and atmospheric background radiance which is electrically connected with said host system, said first calculating means receiving said/slant angles from said host system and conditions under which the atmospheric transmittance and background radiance will be predicted, said conditions including a definition of water and ice cloud verticle profiles, a spectral region of interest and determining therefrom an estimate of atmospheric transmittance and atmospheric background radiance for said slant angles.

* * * * *